(12) United States Patent
Hennig

(10) Patent No.: US 8,471,221 B2
(45) Date of Patent: Jun. 25, 2013

(54) DEVICE FOR MEASURING FLUORESCENT RADIATION ON BIOLOGICAL SUBSTANCES WITH A SEMI-CONDUCTOR SENSOR ARRANGEMENT

(75) Inventor: Thomas Hennig, Langenfeld (DE)

(73) Assignee: Ferton Holding, S.A., Delemont (CH)

(*) Notice: Subject to any disclaimer, the term of this patent is extended or adjusted under 35 U.S.C. 154(b) by 196 days.

(21) Appl. No.: 12/680,964

(22) PCT Filed: Oct. 1, 2008

(86) PCT No.: PCT/EP2008/008330
§ 371 (c)(1),
(2), (4) Date: May 13, 2010

(87) PCT Pub. No.: WO2009/046923
PCT Pub. Date: Apr. 16, 2009

(65) Prior Publication Data
US 2010/0219354 A1   Sep. 2, 2010

(30) Foreign Application Priority Data
Oct. 1, 2007   (DE) .................. 10 2007 047 093

(51) Int. Cl.
*G01N 21/64* (2006.01)
(52) U.S. Cl.
USPC ........................................ 250/461.1
(58) Field of Classification Search
USPC .......................... 250/461.1, 461.2
See application file for complete search history.

(56) References Cited

U.S. PATENT DOCUMENTS

| | | | | |
|---|---|---|---|---|
| 3,916,197 A * | 10/1975 | Fulwyler | ................... | 250/361 R |
| 4,493,420 A * | 1/1985 | Dennis | ................... | 209/587 |
| 5,278,497 A * | 1/1994 | Ariyoshi | ................... | 324/207.21 |
| 5,435,724 A * | 7/1995 | Goodman et al. | ................... | 433/215 |
| 5,635,402 A * | 6/1997 | Alfano et al. | ................... | 436/63 |
| 5,968,035 A * | 10/1999 | Goodman et al. | ................... | 606/12 |
| 6,024,562 A * | 2/2000 | Hibst et al. | ................... | 433/29 |
| 6,028,666 A * | 2/2000 | Boss et al. | ................... | 356/301 |
| 6,188,471 B1 | 2/2001 | Jung et al. | | |

(Continued)

FOREIGN PATENT DOCUMENTS

| DE | 42 00 741 A1 | 7/1993 |
|---|---|---|
| DE | 195 41 686 A1 | 5/1997 |

(Continued)

OTHER PUBLICATIONS

International Search Report dated Feb. 17, 2009 to corresponding international patent application No. PCT/EP2008/008330 filed Oct. 1, 2008, 3 pages.

*Primary Examiner* — Kiho Kim
(74) *Attorney, Agent, or Firm* — Maier & Maier PLLC

(57) ABSTRACT

The invention relates to a device for measuring fluorescent radiation emitted by biological substances, comprising a light source, a capturing unit, an evaluation unit, at least one emission fiber, and at least one detection fiber. Said emission fiber guides excitation radiation to the biological substrate and the detection fiber receives fluorescent radiation and guides it to the evaluation unit. The capturing unit comprises a semiconductor sensor arrangement that detects fluorescent radiation emitted by the biological substance in wave length areas that are separate from each other, are arranged. Data sets of at least two different reference measurements on at least two different biological substances are stored and compared to the measured measurement values to the stored data sets and issues a result relating to the pathological attacks of the examined biological substances and/or relating to the type of examined, biological substances.

25 Claims, 5 Drawing Sheets

U.S. PATENT DOCUMENTS

| | | | |
|---|---|---|---|
| 2003/0156788 A1* | 8/2003 | Henning | 385/31 |
| 2004/0012843 A1* | 1/2004 | Aozasa et al. | 359/337.1 |
| 2004/0163470 A1* | 8/2004 | Babala et al. | 73/514.01 |
| 2005/0272027 A1 | 12/2005 | Cheng et al. | |
| 2007/0153541 A1* | 7/2007 | Bennett et al. | 362/574 |
| 2009/0281025 A1* | 11/2009 | Bhoumik et al. | 514/12 |

FOREIGN PATENT DOCUMENTS

| | | |
|---|---|---|
| DE | 202 09 441 U1 | 9/2002 |
| JP | 2004312571 A * | 11/2004 |
| JP | 2007169337 A * | 7/2007 |
| WO | 03/005892 A | 1/2003 |

* cited by examiner

Distance to the end of the light conductor [μm]

DEVICE FOR MEASURING FLUORESCENT RADIATION ON BIOLOGICAL SUBSTANCES WITH A SEMI-CONDUCTOR SENSOR ARRANGEMENT

RELATED APPLICATIONS

This application claims priority, under 35 U.S.C. §119, to German patent application No.: 10 2007 047 093.4, filed on Oct. 1, 2007, the disclosure of which is incorporated by reference herein in its entirety.

The invention relates to a device for measuring fluorescent radiation on biological substances as defined in the preamble of claim 1.

A device for measuring fluorescent radiation on biological substances is known e.g. from DE-A-42 00 741. Said document discloses a device for detection of caries on teeth, comprising an illumination means for emitting radiation in the wavelength range of 360 to 580 nm onto a tooth. A filter will allow the passage of fluorescent radiation in a wavelength range larger than 620 nm returned by the tooth. The radiation allowed to pass through will be evaluated for detection of caries.

Known from DE-A-195 41 686 is a further device for measurement of fluorescent radiation wherein a light source will emit excitation radiation in a wavelength range between 600 and 670 nm onto a tooth under examination. The fluorescent radiation excited on the tooth will be detected and evaluated in a wavelength range between 670 and 800 nm.

The devices known so far have the disadvantage that, in case of an examination in a range of different or changed biological substances, imprecise results may be obtained.

Thus, it is an object of the invention to provide a device of the initially described type which makes it possible to obtain more-exact measurement results with regard to changes or deviations in the structure of biological substances. Biological substances can be endogenous substances or prosthetic materials.

The above object is achieved by the features of claim 1.

The invention advantageously provides that, in a device of the initially described type, a receiving unit comprises a semiconductor sensor arrangement wherein at least three sensors are arranged within a surface. Said at least three sensors are operative to capture the fluorescent radiation emitted on the biological substance in wavelength ranges that are separated from each other. The evaluation unit can have stored therein different sets of data, preferably in the form of multidimensional measurement values and more preferably three-dimensional measurement values, wherein the evaluation unit will compare the measured measurement values to said sets of data and will output a result relating to the pathological attacks of the examined biological substances and/or relating to the type of examined biological substances. In the evaluation unit, there can have been stored sets of data from at least two different reference measurements on two different biological substances. In order to enable the evaluation unit to issue a result with regard to the type of the examined biological substances, at least three reference measurements must have been stored in the evaluation unit. The result will be displayed by the display unit. Preferably, however, there are provided three or more reference measurements on three or more different biological substances.

The emission and detection fibers can be flexible light conductors as well as rod lenses in an endoscope.

The at least one detection fiber can be arranged with its proximal end preferably centrically above the semiconductor sensor arrangement at a distance from the surface of the semiconductor sensor arrangement.

The invention has the advantage that the sensors used will capture the fluorescent radiation excited on the biological substance, particularly on a biological tissue, in three mutually separated wavelength ranges and that an evaluation unit will evaluate the radiation.

In the previous state of the art, use has been made of the ratios between the measurement signals between the individual sensors to thus be able to obtain a result with regard to the pathological attacks of the examined biological substances. Ratios between the measurement signals of the individual sensors, however, can represent only linear curve developments. Stored reference measurements can also describe non-linear curve developments and can thus yield exact results within a large dynamic range.

The use of more than two reference measurements makes it possible to include a larger spectrum of various possible substances. Thus, for instance, endogenous substances and prosthetic materials have different optical signatures, such as e.g. the fluorescence spectra of the substances, which, however, should be evaluated identically in certain diagnostic analyses.

The deposition of at least three sets of reference data allows for a differentiated diagnostic statement on the type of the substance under examination.

The device of the invention can be used for detection of bacterial attack on teeth. Due to the large number of types of tissue or of tooth materials with different filling materials, an analysis based on three spectral ranges will be significantly more precise and reliable.

The device of the invention can also be used for detection of tumors, particularly malignant tumors, by endoscopic examination. For this purpose, a photoactive substance, preferably 5-aminolevulinic acid (5-ALA) will be introduced into the biological tissue. When excited by an excitation radiation, the biological substance will fluoresce, and the malignant cells will be clearly distinguishable from the healthy tissue. Malignant cells are equivalent to cells of a malignant tumor. However, due to the inherent fluorescence of the skin (autofluorescence), one may happen to obtain wrong results. In an analysis based on three spectral ranges, this autofluorescence is detectable and can be discriminated. In an analysis based on three spectral ranges, a diagnosis possible even without prior introduction of photoactive substances.

In the device of the invention, it can be provided that the light cone exiting from the proximal end of the detection fiber will illuminate the sensor surface of the semiconductor sensor arrangement without interposition of optical lenses.

In comparison to the previous state of the art, this has the advantage that the returned radiation does not have to be guided via separate light conductors to different optical receivers and does not have to be distributed among the optical receivers via mirrors or other optical elements. The light cone exiting from the proximal end of the detection fiber can illuminate the sensor surface without interposition of optical lenses.

With the aid of a light-conductor support, the detection fiber is held centrically above the semiconductor sensor arrangement and at a predetermined distance from the surface of the semiconductor sensor arrangement, said light-conductor support being fastened to the casing of the semiconductor sensor arrangement.

Said three sensors can be sensors for radiations lying in the wavelength ranges of the basic colors red, green and blue, respectively. The three sensors can also be sensors for radiations lying in other wavelength ranges, i.e. in the wavelength radiations of mixed colors.

The sensors can be arranged within a circular surface, and the respective basic color can have assigned thereto a circular surface segment of 120°.

This embodiment has the advantage that the returned radiation will be equally distributed onto the sensors because the detection fiber is positioned centrically to the semiconductor sensor arrangement.

Said three sensors are not restricted to being arranged within a circle but can also be arranged in any desired configuration relative to each other.

The sensor for radiation in the wavelength range of the basic color red has the highest sensitivity and is responsive up to at least 750 nm.

This has the advantage that the red fluorescence, which is weak relative to the green fluorescence, will be intensified so that an electrical crosstalk will be prevented.

The sensors can consist of photoresistors, phototransistors, photodiodes and/or pyroelectric sensors. The sensors can have different spectral sensitivities. The sensors can also be color image sensors, e.g. CCD or CMOS.

An optical prefilter for suppression of excitation radiation can be arranged between the at least one detection fiber and the semiconductor sensor arrangement and be fixed on the semiconductor sensor arrangement with the aid of an optically transparent casting compound.

The thickness of the optical prefilter can be less than 2 mm. The prefilter can be a dielectric filter.

Further, the semiconductor sensor arrangement can be arranged on a conductor plate which is shielded against electromagnetic radiation with the aid of an electrically conductive layer preferably made of copper.

Use can be made of any desired layer which is effective for shielding against electromagnetic radiation.

Between the receiving unit and the evaluation unit, three separate amplifiers can be arranged for amplification of the respective signals of the sensors.

The light source used can be an LED chip.

In contrast to laser devices, LEDs radiate light in a wide opening angle. Normal LEDs mounted on a substrate will thus radiate in all directions.

The transmission of light in a light conductor is performed substantially without a change of the opening angle, which is to say that, when exiting from the light conductor, the light will have the same opening angle as upon entrance.

Thus, in order to be able to realize light with a wide opening angle on the exit end of the emission fibers, it is provided, according to a further embodiment that the incoupling is performed without using optical lenses and that a distance of less than 0.3 mm and preferably of 0 mm exists between the LED chip and the proximal end face of the emission fiber.

By the elimination of optical lenses, significantly larger opening angles can be realized.

Between the LED chip and the proximal end face of the at least one emission fiber, a medium can be arranged which has a refractive index between that of the emission fiber and that of the surface of the LED chip. In this manner, the reflection losses at the transitions will be minimized. Preferably, the medium introduced into the intermediate space is optically transparent.

According to a further embodiment, the proximal end face of the emission fibers adjacent to the light-emitting surface of the LED chip is smaller than the light-emitting surface of the LED chip and is completely covered by the light-emitting surface of the LED chip.

According to a further embodiment, the LED chip is operative to emit light in the UV range and/or the adjacent visible range, preferably violet light in the wavelength range from 390 to 420 nm. The radiation in this wavelength range can very efficiently detect the optical differences between healthy and infected teeth or between malign cells and healthy tissue.

The light source can emit periodically modulated light. The excitation radiation can be modulated in its amplitude, the frequency of the amplitude modulation being about 2 kHz.

Between the receiving unit and the evaluation unit, there can be arranged three separate preamplifiers and/or at least one lock-in amplifier and/or at least one subtractor.

Said subtractor can be a hardware subtractor. This means that the circuit elements of the subtractor consist of concrete component parts, such as e.g. ohmic resistors, capacitors or amplifiers. The advantage of a hardware subtractor resides in that the dynamic range of the measurement is fully available independently from an offset.

According to a further embodiment, the emission fibers as well as the detection fibers can have an acceptance angle larger than 35°. Alternatively, the acceptance angle of the emission and detection fibers can be larger than 40°, preferably larger than 45°.

In previously known devices, the substantially axial emission of the radiation from the respective light conductor has turned out to be disadvantageous because, due to the substantially axial emission of the radiation, a sufficient illumination of linear portions of narrow cavities, e.g. gingival pockets, is not possible. For this reason, previously known devices are provided with additional optical elements at the radiation-exit end of the light conductors, which elements cause a not inconsiderable expenditure in manufacture and will considerably enlarge the total diameters of the light conductors.

The invention has the advantage that, due to the large acceptance angles of the emission as well as the detection fibers, bacterially infected sites or malignant cells in narrow cavities, such as e.g. in gingival pockets, can be detected better even without using additional optical elements.

Said acceptance angle larger than 35° corresponds to an opening angle of at least 70°. The advantage of an acceptance angle larger than 35° resides in that the bundle of emission and detection fibers of the present invention will be capable to illuminate also linear cavities without the need to use additional optical elements. In the inventive emission and detection fibers having an acceptance angle larger than 35°, the maximal intensity which is obtained on a plane surface extending vertically to the light exit surface, is considerably higher than in usual quartz-glass light conductors which are no wide-angle light conductors.

The emission and detection fibers can be provide with a single or multiple coating.

The entire distal end face of the emission and detection fibers can be coupled to the proximal end face of at least one light-conducting element, wherein the light-conducting element can be made of sapphire or a mineral material or plastic and have an acceptance angle larger than 35°. The acceptance angle can also be larger than 40°, preferably larger than 45°. The whole distal end face of the emission and detection fibers and the proximal end face of the light-conducting element can be pressed onto each other by application of a spring force.

Further, the fluorescence signals of the light-conducting element can be detectable by the different sensors of the semiconductor sensor arrangement. By comparing the measuring signals generated by the sensors with the reference data sets of different materials as stored in the evaluation unit, also the material of the at least one light-conducting element is detectable. The evaluation unit can indicate which material the light-conducting element is made of.

This has the advantage that the information on the material that the light-conducting element is made of, can be supplied to software means. Said software means determines, inter alia, the sensitivity with which the measurement values are to be evaluated. The supply of the information to said software means has the advantage that the sensitivity of the measurement can be adapted to the material of the light-conducting element. This is to say that the sensitivity with which the measurement values are evaluated can be adapted to the purpose of the application.

The light-conducting element can be guided within an inspection probe comprising a shaft and a coupling portion. Said inspection probe can be connected to a handle portion, and the connection site between the entire distal end face of the emission and detection fibers and the proximal end face of the light-conducting element can be arranged within the handle portion.

The light-conducting element can be rigid or flexible.

The light-conducting element can be operative for conducting the excitation radiation emitted by the light source via the emission fibers to the biological substance, and also for conducting the fluorescent radiation emitted by the biological substance.

The light-conducting element can consist of a single light conductor or of a plurality of light conductors, i.e. of a light conductor bundle.

The total diameter of the single light conductor or the total diameter of the light conductor bundle can be larger than or equal to the total diameter of the emission and detection fibers.

By way of alternative to using the light-conducting element, the emission and detection fibers can be guided directly, i.e. without interposition of a light-conducting element, to the biological substance, e.g. within an endoscope. Also the emission and detection fibers can be guided at the distal end within an inspection probe comprising a shaft and a coupling portion. Said shaft can be rigid and flexible. It can a also be bendable or curved. The shaft can be designed as a protective hose.

The two above described embodiments with inspection probe will allow for easier handling because, due to the curved shaft, the bundle of emission and detection fibers and respectively the light-conducting element can be easily introduced e.g. into gingival pockets.

The emission and detection fibers can terminate with the distal end of the shaft or project relative to the shaft by maximally about 5 cm.

According to a further embodiment, it is provided that the proximal end of the inspection probe is connectable to a handle portion, wherein the emission and detection fibers can be guided within said handle portion.

This has the advantage that the device can be handled in a more convenient manner because said handle portion allows for a better guidance of the bundle of emission and detection fibers.

Said light source can be arranged within the handle portion.

According to a further embodiment, it is provided that the length of the emission fiber or the total length of the emission fiber and the light-conducting element is less than 60 cm, preferably less than 10 cm.

These embodiments have the advantage that the emitted light does not have to cover long distances from the light source to the biological substance, which is relevant since, in wide-angle light-conductors, the intensity of the radiation will decrease with increasing length of the light conductor.

Embodiments of the invention will be explained in greater detail hereunder with reference to the drawings.

The drawings show the following schematic representations:

Figure 2:
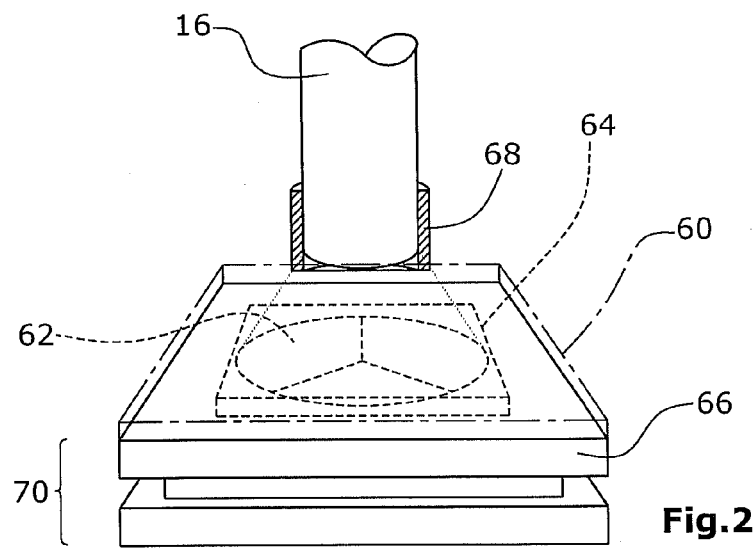
FIG. 2 is a view of a device with a semiconductor sensor arrangement.
Figure 3:
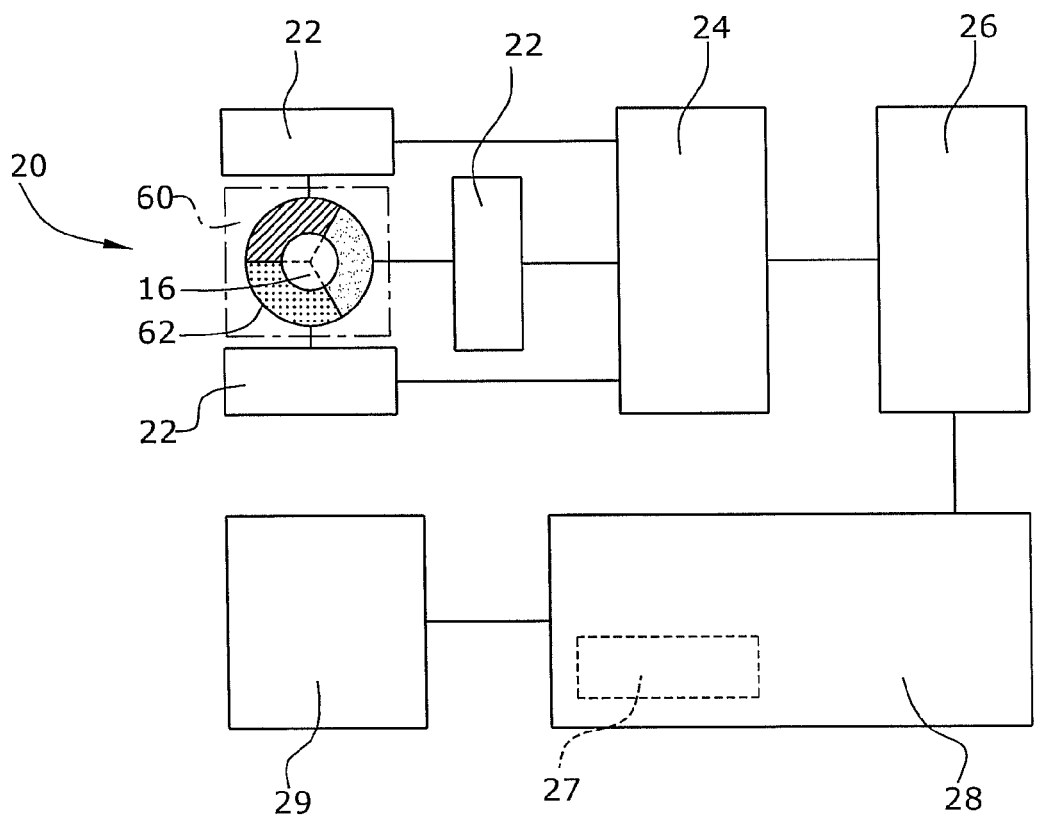
Figure 4:
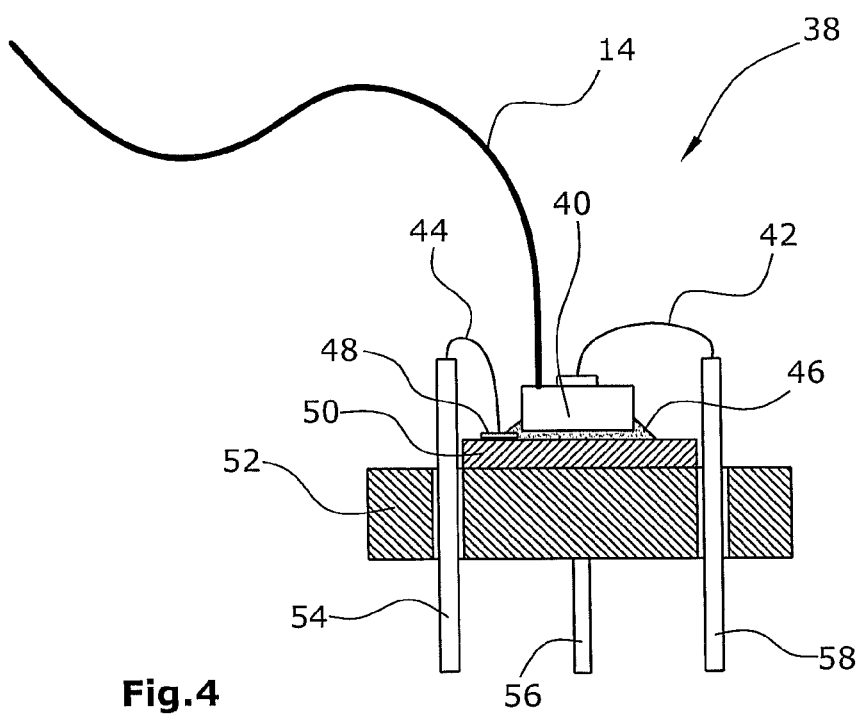
Figure 5:
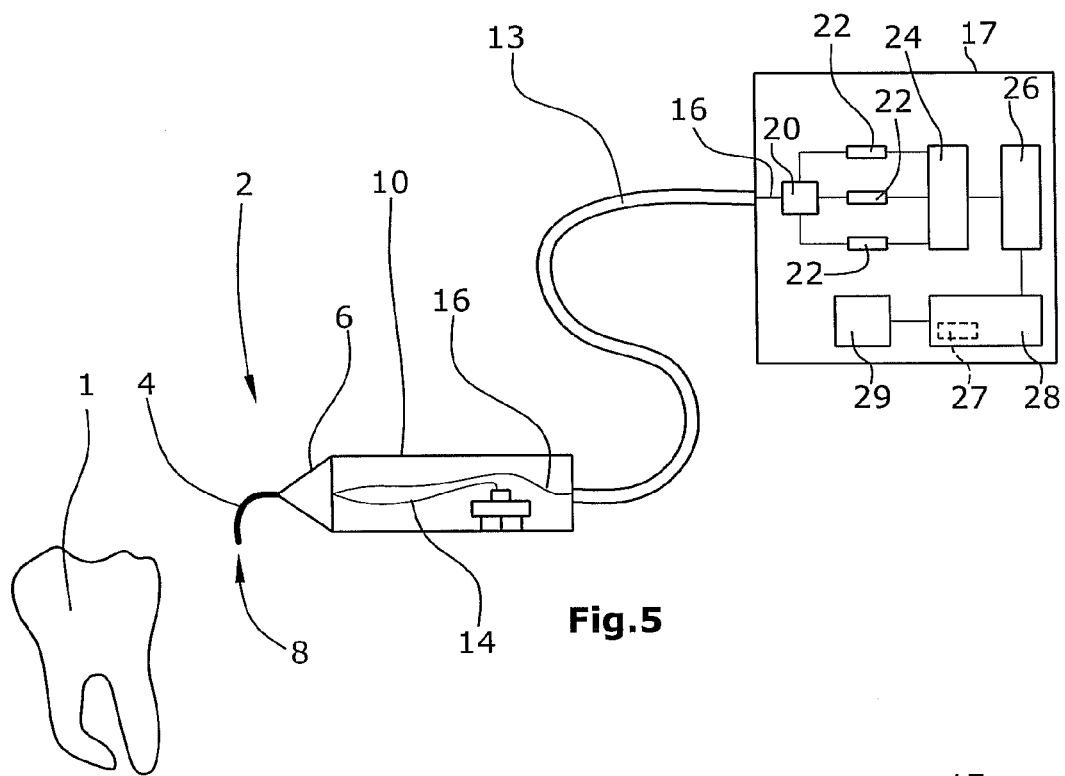
Figure 6:
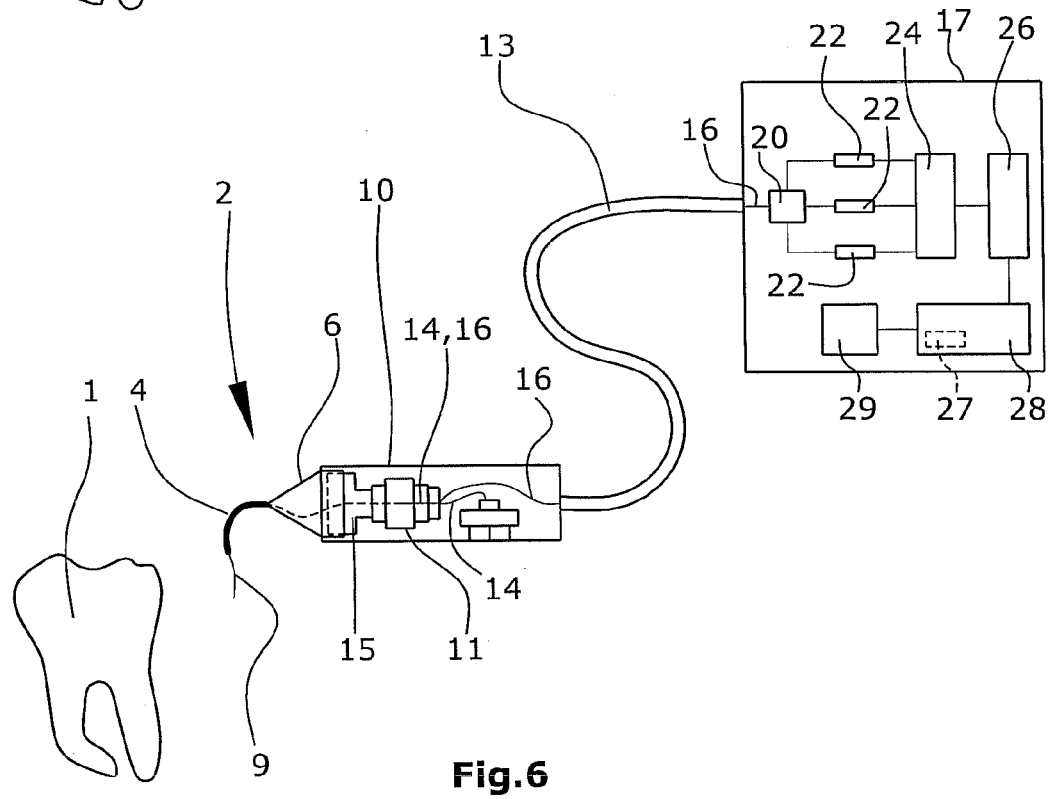
Figure 7A:
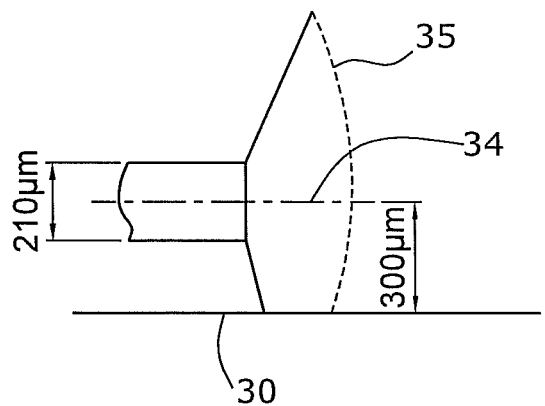
Figure 7B:
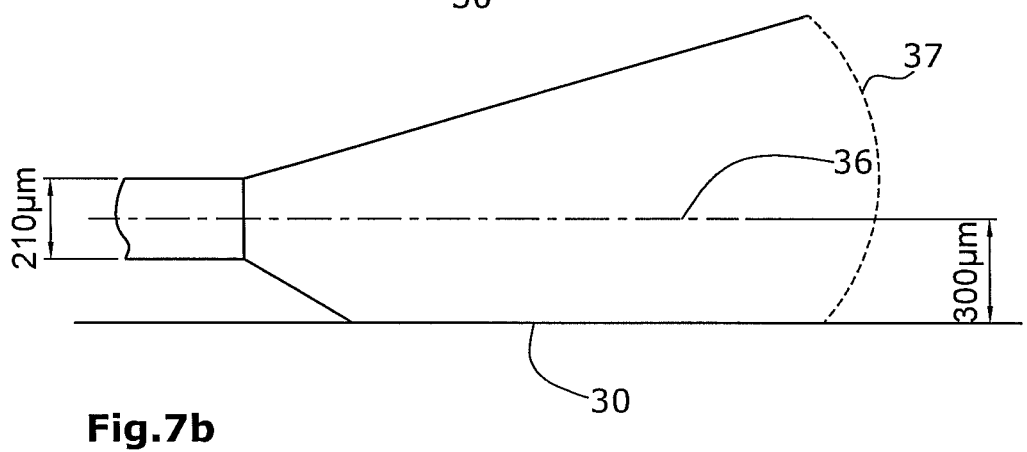
Figure 8:
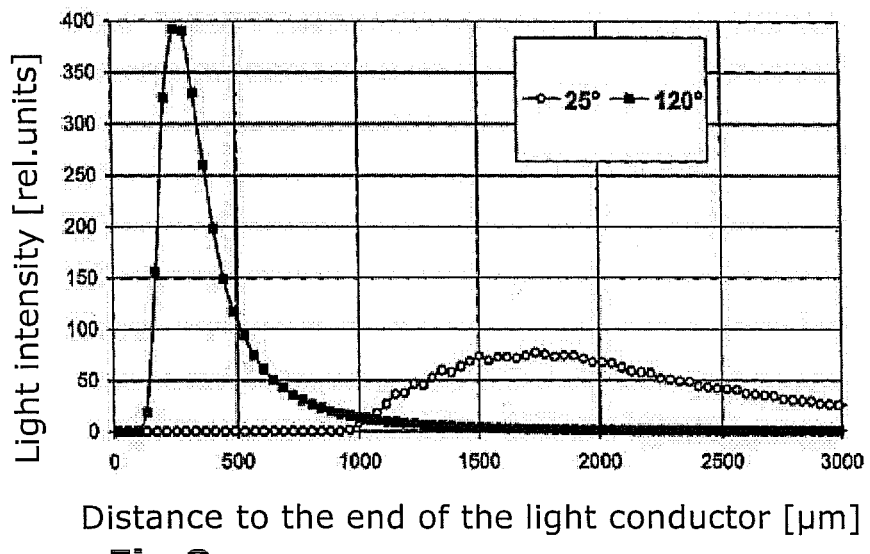
Figure 9:
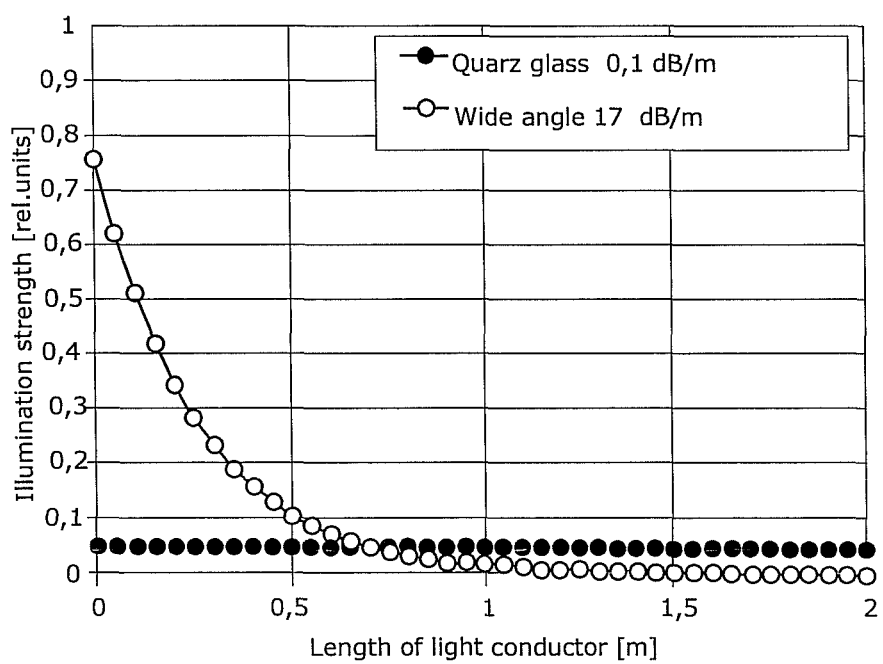

FIG. 3 is a block diagram of the device with receiving unit, amplifier, subtractor, evaluation unit and display unit, FIG. 4 is a view wherein the light source is an LED chip, FIG. 5 is a schematic block diagram wherein the light source is arranged in the handle portion, FIG. 6 is a view of a device with a light-conducting element, FIG. 7a is a view of a wide-angle light conductor whose axis is oriented parallel to a plane surface, FIG. 7b is a view of a quartz-glass light conductor which is not a wide-angle light conductor and whose axis is oriented parallel to the plane surface, FIG. 8 is a diagram of the light distribution on the plane surface of FIG. 2a and FIG. 2b, FIG. 9 is a diagram representing the relationship between the damping of the illumination strength and the length of the light conductor.

Figure 1:
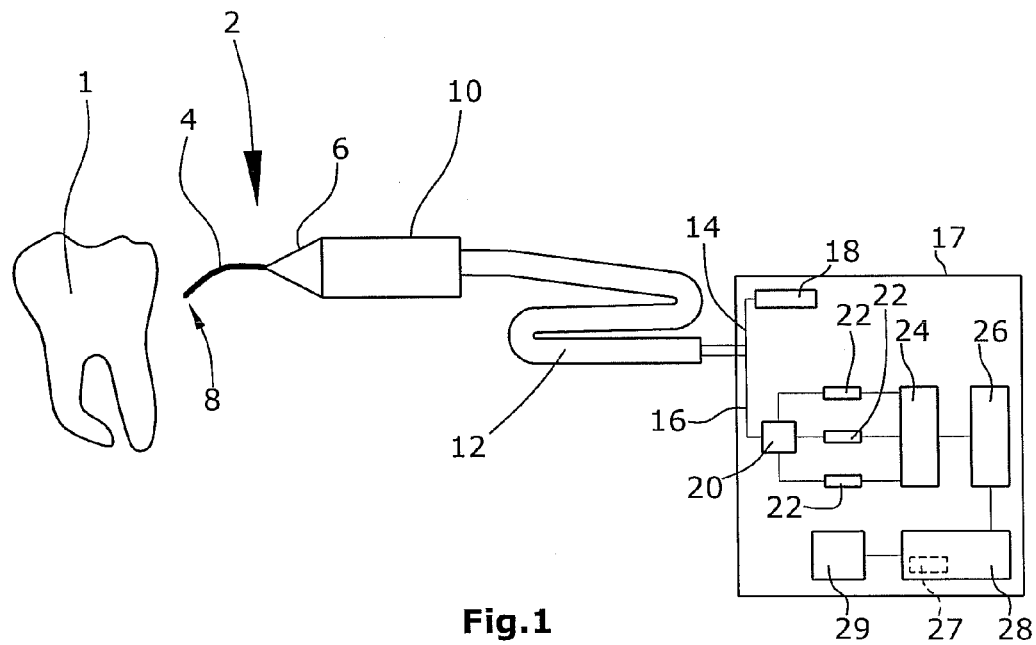
FIG. 1 is a principal block diagram of the device according to the invention.

FIG. 1 shows a principal block diagram of a device according to the invention for use in the field of dentistry. Excitation radiation from a light source 18 will be coupled into a bundle of emission fibers 14 and be transported by these to a tooth 1. Said emission fibers 14 are guided together with detection fibers 16 to a light-conductor cable 12. On its distal end, said light-conductor cable 12 is coupled to a handle portion 10. The emission fibers 14 and the detection fibers 16 are guided in said handle portion 10 and in an inspection probe 2. Said inspection probe 2 comprises a coupling portion 6 and a shaft 4. The proximal end of said coupling portion 6 can be connected to the distal end of handle portion 10. Said shaft 4 is preferably made of metal or plastic. The fluorescent radiation excited by the excitation radiation on the tooth 1 will be transported via detection fibers 16 to a receiving unit 20. On their distal end 8, the emission and detection fibers 14,16 preferably terminate together with the distal end of shaft 4. At the most, the emission and detection fibers 14,16 project by about 5 cm relative to the second shaft.

In said receiving unit 20, the fluorescent radiation will be detected in three mutually separated wavelength ranges and be converted into three electric signals. These will be transmitted, via separate preamplifiers 22, to a lock-in amplifier 24. By means of a subtractor 26, connected downstream of said lock-in amplifier 24, background signals can be subtracted. Background signals are caused by reflection of the excitation radiation at the distal end 8 of the emission and detection fibers 14,16 as well as by a slight inherent fluorescence of the light-conducting fibers and the adhesives used. The amount of the signal is directly proportionate to the excitation radiation. If the excitation radiation is kept constant, a constant offset signal will be obtained. This background signal will be measured during the switch-on routine of the measurement device and will be eliminated in said subtractor 26 prior to evaluation. Within the evaluation unit 28, there is arranged a memory 27 having stored therein the three-dimensional measurement values of healthy tooth material, diseased tooth material and synthetic filling material. The term "three-dimensional" is to be understood in the sense that, for each measurement value, the radiation intensity will be measured in three spectral ranges, e.g. in the spectral ranges of the basic colors red, green, blue. The currently measured three-dimensional measurement value will be compared to the stored comparative measurement values, and the distances to the closest comparative measurement value of healthy tooth material and/or synthetic filling material and diseased tooth material will be determined. The ratio of the distance between the currently measured measurement value and the closest comparative measurement value of healthy tooth material and synthetic filling material and the distance between the currently measured measurement value and the closest comparative measurement value of diseased tooth material, will be indicated in the form of values on a display unit 29. The user will know that, if this value is smaller than a certain value, the examined tooth region is free of bacterial remnants.

The inventive device for detection of tumors, particularly malignant tumors, is of a design similar to that of the device described in connection with FIG. 1. A difference consists in that there are used no handle portion 10 and no inspection probe 2. The light-conductor cable 12 has its distal end coupled to an endoscope. The emission and detection fibers 14,16 are guided within said endoscope and terminate, on their distal end, together with the distal end of the endoscope, or are arranged to project by maximally about 5 cm beyond the distal end of the endoscope. The endoscope can be introduced into the human body, e.g. for examination of the bladder or for examination of other cavities of the body.

FIG. 2 shows a bundle of detection fibers 16 which, via a semiconductor sensor arrangement 62 according to the invention and at a defined distance from the surface of the semiconductor sensor arrangement 62, are centrically positioned with the aid of a light conductor support 68. Said light conductor support 68 is fastened, although not shown here, to the casing of the semiconductor sensor arrangement 62. The semiconductor sensor arrangement 62 comprises three sensors, arranged within a circle, by which the fluorescent radiation excited on the tooth via the emission fibers 14 will be captured in three mutually separated wavelength ranges and will be converted into three electric signals. Said three sensors are sensors for the basic colors red, green and blue. Each of said basic colors has a circular segment of 120° assigned thereto. The distance between the end face of the detection fibers 16 and the surface of the semiconductor sensor arrangement 62 will safeguard a complete illumination of the three sensors. When using wide-angle light conductors, the distance between the end face of the detection fibers 16 and the surface of the semiconductor sensor arrangement 62 can be less than 2 mm. Between the detection fibers 16 and the semiconductor sensor arrangement 62, a prefilter 64 for suppressing the excitation radiation can be arranged. Said prefilter 64 is fixed on the semiconductor sensor arrangement 62 with the aid of an optically transparent casting compound.

FIG. 3 shows a block diagram of the device of the invention. The detection fibers 16 for conducting the radiation returned by the tooth are centrally positioned above a semiconductor sensor arrangement 62 at a defined distance from the semiconductor sensor arrangement 62. The semiconductor sensor arrangement 62 comprises three sensors arranged within a circle and operative to capture, in three mutually separated wavelength ranges, the fluorescent radiation excited on the tooth or in the gingival pocket via the emission fibers 14 and to convert this radiation into three electric signals. As depicted in FIG. 1, these signals will be supplied via separate preamplifiers 22, a lock-in amplifier 24 and a subtractor 26 to an evaluation unit 28. There, the measurement values will be compared to comparative measurement values stored in a memory 27, and a value will be output which can be displayed on a display unit 29. If said value is above a certain value, this will indicate that the tooth is bacterially infected.

FIG. 4 shows an LED chip 40 connected opposite to the emission fibers 14. This is to say that, between the surface of the LED chip and the proximal end face of the emission fibers 14, there remains a distance being less than 0.3 mm and preferably being 0 mm. Between the LED chip surface and the emission fibers 14, a preferably transparent medium, e.g. synthetic resin, not shown, can be arranged which has a refractive index between that of the emission fibers 14 and that of the LED chip surface. With the aid of said transparent medium, e.g. a curable plastic, the emission fibers are mechanically tightly fastened to LED chip 40 and optically coupled thereto. By use of an electrically conductive adhesive 46, LED chip 40 is mounted to a monitor diode chip 50 and electrically contacted thereto. Said monitor diode chip 50 delivers a measurement value which is proportionate to the optical output performance of LED chip 40. From an electric contact site 48, a bond wire 44 is connected to an electric connection pin 54 guided in an insulating manner in the socket 52. Said monitor diode 50 comprises a second electric contact in the form of a housing pin 56 which is guided to the outside. Also LED chip 40 comprises a second electric connection. This connection is realized via a bond wire 42 which is connected to an electric connection pin 58 guided in an insulating manner in the socket 52.

Alternatively, the arrangement according to FIG. 4 can also be realized without the monitor diode 40. In this case, said electric contact site 48 and said bond wire 44 with said pin 54 insulated within said socket would be omitted.

To keep the radiation losses of the excitation radiation low, one embodiment, shown in FIG. 5, which is similar to the embodiment of FIG. 1, provides that the light source is arranged within handle portion 10. This has the advantage that the emission fibers 14 can be realized with a very short length. The emission fibers 14 and the detection fibers 16 are joined at the distal end of handle portion 10. Following at the distal end is an inspection probe with shaft and coupling member, with the emission fibers 14 and the detection fibers 16 being guided therein. Distally, the emission and detection fibers terminate together with the distal end of the shaft. The fluorescent radiation excited on the tooth 1 will be transmitted from tooth 1 via the detection fibers 16 to a receiving unit 20 located within device 17. The detection fibers 16 are guided, from the proximal handle portion 10 to the receiving unit 20, in the light conductor cable 13. In FIG. 5, there is used the light source from FIG. 4.

FIG. 6 shows a block diagram which is very similar the one in FIG. 5, with the difference that the end face of the bundle of emission and detection fibers is coupled to the end face of a light-conducting element 9.

Said light-conducting element 9 is guided within a centering device 15 and projects from the proximal end of said centering device 15 from the latter. The centering device 15 and thus the light-conducting element 9, together with the bundle of emission and detection fibers 14,16, are pressed against each other within a plug and coupling element 11 by means of a spring. Such a plug and coupling element 11 can be a commercially available ST plug provided with a bayonet catch. Said plug and coupling element 11 is arranged internally of handle portion 10. The light-conducting element 9 is pressed back into the first coupling member 7 by the length projecting relative to the proximal end of the centering device 15. Since the light-conducting element 9 is fixed or bonded within the shaft 4 and/or the distal end of coupling member 6, the light-conducting element 9 which in this case is a flexible light-conducting fiber made of plastic, is bent within the coupling member 6. By said bending, the light-conducting element 9 is subjected to tension, with the effect that the light-conducting element 9 is permanently pressed against the bundle of emission and detection fibers 14,16. This will safeguard a good incoupling of the radiation from the bundle of emission and detection fibers 14,16 into the light-conducting element 9, and vice versa.

At the connection site, the excitation radiation from the emission fiber 14 will be coupled into the light-conducting element 9. The light-conducting element 9 is guided within an injection probe 2. Said injection probe 2 comprises a shaft 4 and a coupling member 6. The light-conducting element 9 can terminate at its distal end together with the distal end of said shaft 4 or distally project therefrom, extending from the first shaft 5 maximally by 30 mm. The light distally exiting from the light-conducting element 9 will illuminate the tooth portion under examination. The light returned by the tooth portion under examination will be received by the distal end of the light-conducting element 9 and be guided to a receiving unit 20 via the detection fibers 16.

Alternatively, the light-conducting element 9 can also be made of sapphire or other mineral materials. The connection between the light-conducting element 9 and the bundle of emission and detection fibers 14,16 can also be realized without bending the light-conducting element 9, especially if the light-conducting element 9 is rigid. The light-conducting element 9 and the bundle of emission and detection fibers 14,16 can have a spherical end face so as to achieve a better incoupling of the light.

Further, the light-conducting element can consist of a plurality of light conductors, i.e. the light-conducting element consists of light conductor bundle. These light conductors have each have a diameter of about 30 μm. Also these light conductors can be made of sapphire or other mineral materials or plastics.

Further, in addition to the fluorescence signals of the illuminated tooth portions, also the fluorescence signals of the light-conducting element 9 can be received by the receiving unit 20. Also these latter fluorescence signals will then be converted into electric signals. Via separate preamplifiers 22, a lock-in amplifier 24 and a subtractor 26, these signals will be supplied to evaluation unit 28. Within the memory 27 which is located internally of evaluation unit 28, there can additionally be deposited three-dimensional measurement values of the materials of various possible light-conducting elements 9. The measured fluorescence signals of the light-conducting element 9 can be compared to the stored measurement values. In this manner, it can be detected of which material the light-conducting element 9 is made. The sensitivity of the measurement can be adapted to the material of the light-conducting element.

An inventive device for detection of tumors, particularly malignant tumors, is of a design similar to that of the devices described in connection with FIGS. 5 and 6. A difference resides in that no inspection probe 2 is used. An endoscope is coupled to the distal end of handle portion 10. The emission and detection fibers 14,16 are guided within the endoscope and terminate, on the distal end, together with the distal end of the endoscope, and they are arranged to project by maximally about 5 cm beyond the distal end of the endoscope. The endoscope can be introduced into the human body for examination of cavities of the body.

FIGS. 7a and 7b show a light cone representing a wide-angle light conductor, and, for comparison thereto, the light cone of a common quarts-glass light conductor which is not a wide-angle light conductor. The central axes 34,36 of the two light conductors are arranged at a distance of 300 μm in parallel to a plane surface 30. The diameters of the light conductors are 210 μm in each case. The wide-angle light conductor will irradiate the light with an opening angle of 120° which corresponds to an acceptance angle of 60°. A conventional cone of a common quarts-glass light conductor which is not a wide-angle light conductor has an opening angle of 25°. The light intensities on the plane surface 30 are highest in those regions where the lines 35 and 37 are incident on the plane surface 30.

Preferably, the wide-angle light conductors used are glass light conductors having an acceptance angle larger than 35°, preferably larger than 40°. However, one can also use wide-angle light-conductive fibers made of plastic, preferably of polystyrene.

FIG. 8 shows the light distributions on the plane surface 30 of FIGS. 7a and 7b. The light-exit surface, i.e. the free end of the light conductors, is located at the value 0 on the abscissa. The white dots represent the light intensity distribution for common quartz-glass light conductors having an opening angle of 25°, and the black squares represent the light intensity distribution for wide-angle light conductors having an opening angle of 120°. One can see clear differences between the two curves. An opening angle of only 25° will lead to a flat shape of the curve. The maximal light intensity obtained on the plane surface 30 has a distance substantially between 1.5 mm and 2 mm from the light exit surface of the light conductor end at an opening angle of 25°. In case of an opening angle of 120°, the maximal light intensity obtained on the plane surface 30 has a distance of only about 0.3 mm from the light exit end. In the case of the wide-angle light conductor as used in the device according to the invention, the maximum intensity achieved on the plane surface is more than five times higher than the maximum intensity of a usual quartz glass light conductor which is not a wide-angle light conductor. This has the consequence that distinctly more-accurate measurement values can be obtained because the signal/noise ratio is considerably better. In a wide-angle light conductor, the examined surface portion is significantly shorter and better illuminated than in usual quartz glass light conductors which are no wide-angle light conductors, as evident from FIGS. 7a and 7b. The ratio between the bacterially infected surface and the examined surface portion has a direct influence on the measurement values, which is to say that, if the bacterially infected surface is small in comparison to the examined surface portion, the contamination can be read from the measurement values only with difficulties, which is due to the small percentage of the contaminated surface relative to the total surface portion under examination. Thus, as evident from FIG. 8, when using normal quartz-glass light conductors with large examined surfaces and weak illumination, smaller contaminated areas can easily happen to be overlooked. In wide-angle light conductors with a relatively short surface portion and intense illumination, the ratio between the contaminated surface and the examined surface portion with regard to the percentage is more favorable so that contaminated surfaces can be detected more distinctly and accurately. For this reason, the examined tooth portions, particularly in narrow cavities, can be examined with greater accuracy when using the wide-angle light conductor of the invention.

FIG. 9 shows the illumination strength at the end of various light conductors relative to the illumination strength at the entrance to the light conductors in dependence on the length of the light conductors. The relative illumination strength was calculated according to the following formula:

$$B = NA^2 * 10^{-((a*L)/10)}$$

B: illumination strength
NA: numerical aperture
a: damping of the light-conductor in dB/m
L: length of the light-conductor in m The open circles relate to a wide-angle light conductor with an opening angle of 120°. In the range of 400 nm, this wide-angle light conductor has a damping of about 17 dB/m. The black dots relate to a quartz-glass light conductor with an opening angle of 25°. In the range of 400 nm, this quartz-glass light conductor has a damping of about 0.1 dB/m.

From FIG. 9, it is evident that, especially in wide-angle light conductors, long light-conducting fibers will cause a weakening of the light available on the exit surface, which is the case particularly in the short-wave spectral range around 390-420 nm that is of interest for fluorescence excitation. To avoid this damping effect, the light-conducting fibers, in case that a wide-angle light conductor is used, should have a length of less than 60 cm, preferably less than 10 cm. In this manner, it is made possible, in contrast to the usual quartz-glass light conductors which are no wide-angle light conductors, to accomplish an illumination strength that is about 10 times higher.

The invention claimed is:

1. A device for measuring fluorescent radiation emitted by biological substances, said device comprising:
a light source,
a receiving unit,
an evaluation unit that is coupled to the receiving unit,
at least one emission fiber coupled to the light source, and at least one detection fiber coupled to the receiving unit, said emission fiber guiding excitation radiation to the biological substance, and the detection fiber receiving the fluorescent radiation excited on the biological substance and guiding said radiation to the evaluation unit,
wherein the receiving unit further comprises a semiconductor sensor arrangement in which at least three sensors are arranged inside a surface for detecting fluorescent radiation emitted by the biological substance in wave length ranges that are separate from each other, the evaluation unit having stored therein data sets of at least two different reference measurements on at least two different biological substances, and the evaluation unit comparing the measured measurement values to the stored data sets and outputting a result relating to the pathological attacks of the examined biological substances and/or relating to the type of examined biological substances,
wherein said data sets are stored in the form of multi-dimensional measurement values,
wherein for each measurement value, the radiation intensity will be measured in multi spectral ranges.

2. The device according to claim 1, wherein the light cone exiting from the proximal end of the detection fiber illuminates the sensor surface of the semiconductor sensor arrangement without interposition of optical lenses.

3. The device according to claim 1, wherein the detection fiber is fixed above the semiconductor sensor arrangement and at a distance from the surface of the semiconductor sensor arrangement with the aid of a light-conductor support, said light-conductor support being fastened to the casing of the semiconductor sensor arrangement.

4. The device according to claim 1, wherein the three sensors are sensors for the basic colors red, green and blue, said sensors being arranged within a circular surface and each of said basic colors having assigned thereto a circular surface segment of 120°.

5. The device according to claim 1, wherein the sensor for the basic color red has the highest sensitivity and is responsive up to at least 750 nm.

6. The device according to claim 1, wherein the sensors can comprise photoresistors, phototransistors, photodiodes and pyroelectric sensors, said sensors having different spectral sensitivities.

7. The device according to claim 1, wherein an optical prefilter for suppression of excitation radiation is arranged between the at least one detection fiber and the semiconductor sensor arrangement and is fixed on the semiconductor sensor arrangement with the aid of an optically transparent casting compound.

8. The device according to claim 7, wherein the thickness of the optical prefilter is less than 2 mm.

9. The device according to claim 7, wherein the prefilter is a dielectric filter.

10. The device according to claim 1, wherein the semiconductor sensor arrangement is arranged on a conductor plate which is shielded against electromagnetic radiation with the aid of an electrically conductive layer preferably made of copper.

11. The device according to claim 1, wherein, between the receiving unit and the evaluation unit, three separate amplifiers are arranged for amplification of the respective signals of the sensors.

12. The device according to claim 1, wherein the light source is an LED chip.

13. The device according to claim 12, wherein the LED chip is operative to emit light in the UV range and in the visible range, preferably violet light in the wavelength range from 390 nm to 420 nm.

14. The device according to claim 1, wherein the light source is operative to emit periodically modulated light and the frequency of the amplitude modulation is about 2 kHz.

15. The device according to claim 1, wherein, between the receiving unit and the evaluation unit, three separate preamplifiers and at least one lock-in amplifier and at least one subtractor are arranged.

16. The device according to claim 15, wherein said subtractor is a hardware subtractor.

17. The device according to claim 1, wherein the emission fibers as well as the detection fibers have an acceptance angle larger than 35°, preferably larger than 45°.

18. The device according to claim 1, wherein the entire distal end face of the at least one emission fiber and of the at least one detection fiber is coupled to the proximal end face of at least one light-conducting element, said light-conducting element comprising a single light conductor or of a bundle of light conductors.

19. The device according to claim 18, wherein the light-conducting element is guided within an inspection probe comprising a shaft and a coupling member.

20. The device according to claim 19, wherein the proximal end of the inspection probe can be connected to a handle portion, the light source being arranged within said handle portion.

21. The device according to claim 1, wherein the length of the at least one emission fiber or the total length of the at least one emission fiber and of the light-conducting element is less than 60 cm, preferably less than 10 cm.

22. The device according to claim 1, wherein the emission and detection fibers are guided at the distal end within an inspection probe comprising a shaft and a coupling portion.

23. The device according to claim 1, wherein the data set is in the form of a three-dimensional measurement values, and the radiation intensity will be measured in three spectral ranges.

24. A device for measuring fluorescent radiation emitted by biological substances, said device comprising:
- a light source;
- a receiving unit;
- an evaluation unit that is coupled to the receiving unit;
- at least one emission fiber coupled to the light source, and at least one detection fiber coupled to the receiving unit, said emission fiber guiding excitation radiation to the biological substance, and the detection fiber receiving the fluorescent radiation excited on the biological substance and guiding said radiation to the evaluation unit,
- wherein the receiving unit further comprises a semiconductor sensor arrangement in which at least three sensors are arranged inside a surface for detecting fluorescent radiation emitted by the biological substance in wave length ranges that are separate from each other, the evaluation unit having stored therein data sets of at least two different reference measurements on at least two different biological substances, and the evaluation unit comparing the measured measurement values to the stored data sets and outputting a result relating to the pathological attacks of the examined biological substances and/or relating to the type of examined biological substances,
- wherein said data sets are stored in the form of multi-dimensional measurement values,
- wherein for each measurement value, the radiation intensity will be measured in multi spectral ranges,
- wherein the entire distal end face of the at least one emission fiber and of the at least one detection fiber is coupled to the proximal end face of at least one light-conducting element, said light-conducting element comprising a single light conductor or of a bundle of light conductors,
- wherein the fluorescence signals of the light-conducting element are detectable by the three sensors of the semiconductor sensor arrangement and that, by comparing the measuring signals generated by the three sensors with the reference data sets of different materials as stored in the evaluation unit, also the material of the light-conducting element is detectable and the evaluation unit indicates which material the light-conducting element is made of.

25. The device according to claim 24, wherein the sensitivity of the measurement is adapted to the material of the light-conducting element.

* * * * *